United States Patent [19]

Sting et al.

[11] Patent Number: 5,703,366
[45] Date of Patent: Dec. 30, 1997

[54] OPTICAL SENSING WITH CRYSTAL ASSEMBLY SENSING TIP

[75] Inventors: Donald W. Sting, New Canaan, Conn.; Milan Milosevic, Fishkill, N.Y.

[73] Assignee: ASI Applied Systems, L.L.C., Norwalk, Conn.

[*] Notice: The term of this patent shall not extend beyond the expiration date of Pat. No. 5,552,609.

[21] Appl. No.: 706,169

[22] Filed: Aug. 30, 1996

Related U.S. Application Data

[63] Continuation of Ser. No. 242,360, May 13, 1994, Pat. No. 5,552,604.

[51] Int. Cl.$^6$ .................................................. G01N 21/00
[52] U.S. Cl. ........................... 250/341.2; 250/341.8; 250/339.11
[58] Field of Search ...................... 250/341.2, 341.8, 250/339.11

[56] References Cited

U.S. PATENT DOCUMENTS

| | | | |
|---|---|---|---|
| 3,141,094 | 7/1964 | Strickler. | |
| 3,164,663 | 1/1965 | Gale. | |
| 3,370,502 | 2/1968 | Wilks, Jr.. | |
| 3,733,130 | 5/1973 | Young | 356/246 |
| 3,751,672 | 8/1973 | Michel et al.. | |
| 4,595,833 | 6/1986 | Sting | 250/353 |
| 4,654,532 | 3/1987 | Hirschfeld | 250/458.1 |
| 4,730,882 | 3/1988 | Messerschmidt | 356/300 |
| 4,784,488 | 11/1988 | Doyle et al.. | |
| 4,810,093 | 3/1989 | Doyle. | |
| 4,812,041 | 3/1989 | Doyle. | |
| 4,826,313 | 5/1989 | Schar et al. | 250/343 |
| 4,829,186 | 5/1989 | McLachlan et al. | 250/373 |
| 4,835,389 | 5/1989 | Doyle | 250/343 |
| 4,886,357 | 12/1989 | Harrick | 356/300 |
| 4,988,195 | 1/1991 | Doyle | 356/300 |
| 5,051,551 | 9/1991 | Doyle | 250/343 |
| 5,185,834 | 2/1993 | Day et al. | 385/47 |
| 5,200,609 | 4/1993 | Sting et al. | 250/343 |
| 5,218,656 | 6/1993 | Day et al. | 385/47 |
| 5,220,401 | 6/1993 | Milosevic et al. | 356/300 |
| 5,459,316 | 10/1995 | Doyle | 250/339.11 |
| 5,569,921 | 10/1996 | Sato et al. | 250/341.2 |

FOREIGN PATENT DOCUMENTS

A 0056401 3/1989 Japan.

OTHER PUBLICATIONS

Advertisement—A New FTIR Sampling Capability. The Dipper–210 Universal Immersion Sampling System... Your first choice for quick and accurate FTIR analysis of liquids, postes, mulls, and even powders. Axiom Analytical Incorporated.

(List continued on next page.)

*Primary Examiner*—Don Wong
*Attorney, Agent, or Firm*—Calfee, Halter & Griswold

[57] ABSTRACT

A crystal assembly for optical analyzation of samples includes a first crystal member and a second crystal member, the latter of which is preferably a diamond. The first and second crystal members, which have substantially the same index of refraction for infrared energy, are coupled together at an optically transmitting interface. This interface may be formed by crystal surfaces in intimate contact with one another or by a third crystal member positioned therebetween. The first crystal member has at least one circumferential sidewall focusing surface for redirecting infrared energy within the first crystal member to and from a focal ring or focal plane at or near the optical interface. The focused infrared energy transmitted from the first crystal member is internally reflected within the second crystal member to obtain encoding specific to a sample in contact with a surface of the second crystal member. The encoded infrared energy is then reflected back into the first crystal member for ultimate transmission to a detector.

55 Claims, 6 Drawing Sheets

OTHER PUBLICATIONS

Pharmaceutical process development and optimization using in-situ Fourier transform infrared spectroscopy, Alan J. Rein, Spectra-Tech Applied Systems, Inc., SPIE vol. 1681, pp. 374–380.

In-situ monitoring of chemical reactions by Fourier transform IR spectroscopy, Alan J. Rein, Spectra-Tech Applied Systems, Inc., SPIE vol. 1681, pp. 294–303.

Designing Robust Sample Interfacing Equipment for Infrared Process Analysis, W.M. Doye and N.A. Jennings, Axiom Analytical, Inc.

Principles and applications of Fourier transform infrared (FTIR) process analysis, W.M. Doyle, Axiom Analytical, Inc., Sep. 19, 1991.

Fourier Transform—Infrared Chemical Reaction Monitoring Using an In Situ Deep Immersion Probe, Walter M. Doyle and Norman A. Jennings, Spectroscopy, Val. 5, No. 1, Jan. 1990.

Chemical Composition Monitoring Using An In-Situ Infrared Probe, W.M. Doyle, Proceedings of the ISA 90 International Conference, Paper 490.

Batch Reaction Monitoring Using Process FT-IR-ATR Spectroscopy, Bruce MacIntosh, Spectroscopy, Nov./Dec. 1991, pp. 46–49.

A New Internal Reflection Element Design for High Optical Throughput in FT-IR, Robert G. Messerschmidt, Spectra-Tech, Inc. Stamford, Connecticut, Applied Spectroscopy, vol. 40, No. 5, 1986.

OPTICAL SENSING WITH CRYSTAL ASSEMBLY SENSING TIP

RELATED APPLICATIONS

This is a continuation of application Ser. No. 08/242,360, filed on May 13, 1994, now U.S. Pat. No. 5,552,604.

FIELD OF THE INVENTION

The present invention relates to an optical system with sensor for infrared analysis of samples in general and to a crystal assembly in a small diameter probe tip in particular.

BACKGROUND OF THE INVENTION

Probes utilized as the sample sensing component of an optical system for FTIR analysis are well known in the art. Such probes are utilized in numerous applications, such as placement into an autoclave vessel, where space is restricted and/or weight and size represent functional and economic problems.

Probes that are currently on the market suffer from one or more of the following problems:

1. Probes are typically large when compared to sensors using other sensing techniques;
2. The infrared sensor materials are typically relatively expensive;
3. The infrared sensor materials do not have particularly good chemical resistivity properties or mechanical properties;
4. The infrared sensor surface is difficult to clean and requires a great deal of care to assemble and use;
5. Some probes have very short sampling path lengths; and
6. Infrared detectors frequently have limited energy throughput resulting in the optical system being energy starved or deprived.

The probe and sensor crystal assembly of the present invention are designed to eliminate or reduce the magnitude of these problems.

SUMMARY OF THE INVENTION

A principal object of the present invention is to improve energy throughput and optical sampling sensitivity. By so doing, the probe having the crystal assembly and structure disclosed herein presents the detector with a stronger signal in order to improve signal to noise performance in the optical system.

Another object of the present invention is to improve the chemical resistivity and mechanical properties of the probe tip sensor while providing an easily cleaned and easily optically polished crystal sensor material. To achieve this purpose, the present invention preferably uses a very thin diamond wafer as the sample sensing member in the crystal assembly. The diamond wafer has a surface in contact with the sample and has infrared energy transmitted therethrough, preferably in multiple internal reflections. By using the preferred crystal assembly, one crystal member may be less expensive and more easily formed, while the second crystal member of diamond can be smaller and more rugged and robust.

Another object of the present invention is to provide a crystal assembly having at least two members with substantially matching indices of refraction for infrared energy. These indices of refraction are greater than the index of refraction for the infrared energy waveguide or probe tube. By utilizing this difference in the respective indices of refraction, the crystal assembly may have a corrective effect on infrared energy divergence in the collimated or nearly collimated beam delivered to the crystal assembly, while having good optical transmission characteristics within the assembly itself. The collimated or nearly collimated beam of energy enters the crystal assembly through and normal to a flat surface to optimize energy throughput while minimizing any chromatic aberrations.

Yet another object of the present invention is to have a crystal assembly in which a first crystal member has at least one circumferential "sidewall" focusing surface thereon. This circumferential focusing surface reflects input and output energy to and from focal rings or planes at or adjacent the optically transmissive interface between the first and second crystal members. The circumferential focusing surface minimizes the angular spread of energy within the sensor in general and at the sample sensing surface in particular, while maximizing the energy density and sensitivity.

It is still another object of the invention to have a crystal assembly utilizing three crystal members. The third crystal member can be composed of a thin layer or layers between the first and second crystal members to enhance optical transmission therebetween. Alternatively, the third crystal member can be a center disc utilized in conjunction with the second crystal member to increase the infrared energy path length of the multiple internal reflections during sampling.

These and other objects and advantages of the present invention will become apparent as the following description proceeds.

DETAILED DESCRIPTION OF THE PREFERRED EMBODIMENTS

Figure 1:
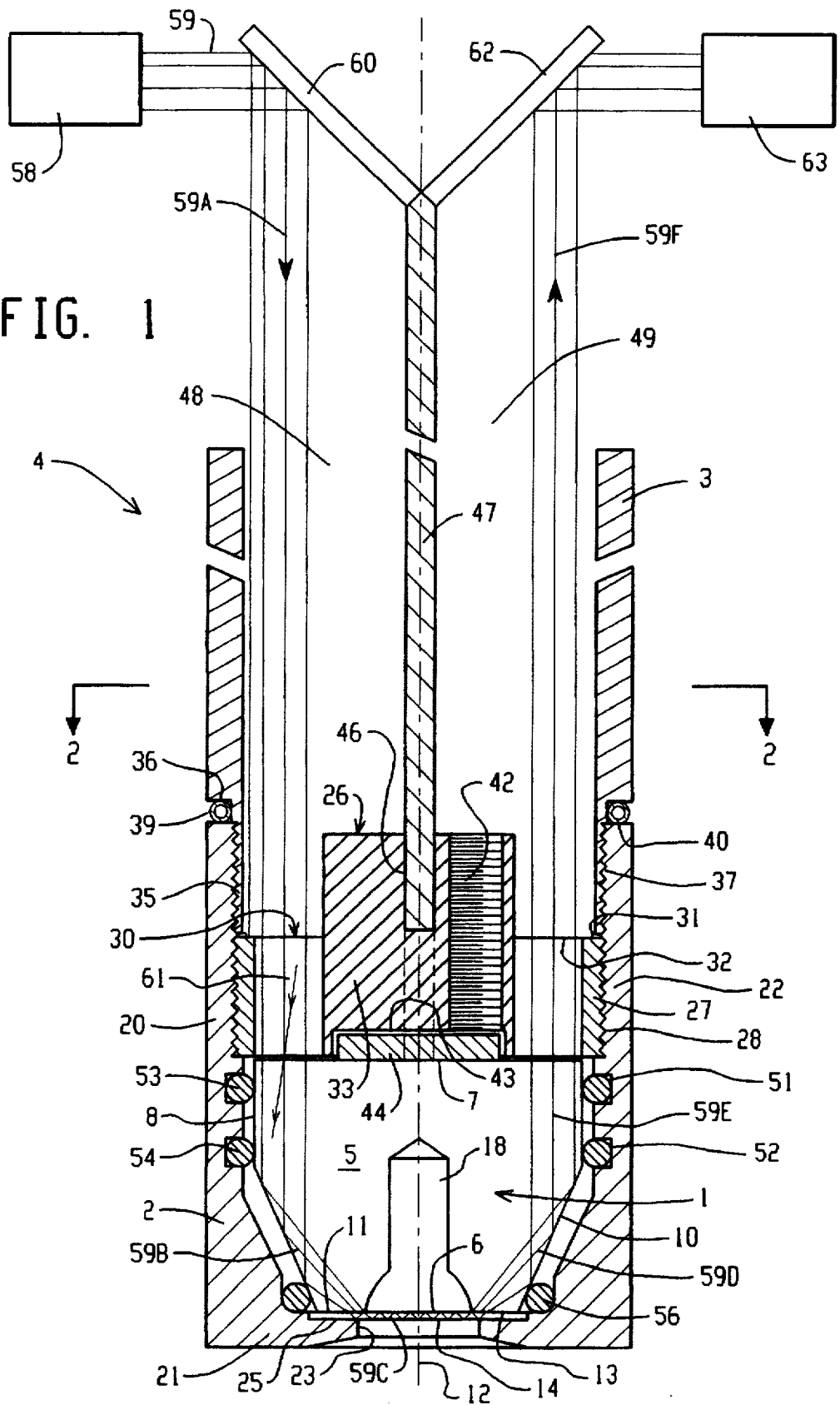
FIG. 1 is an elevation partially in section of a preferred crystal assembly embodiment positioned within the end of a probe in an optical sample analyzation system.
Figure 2:
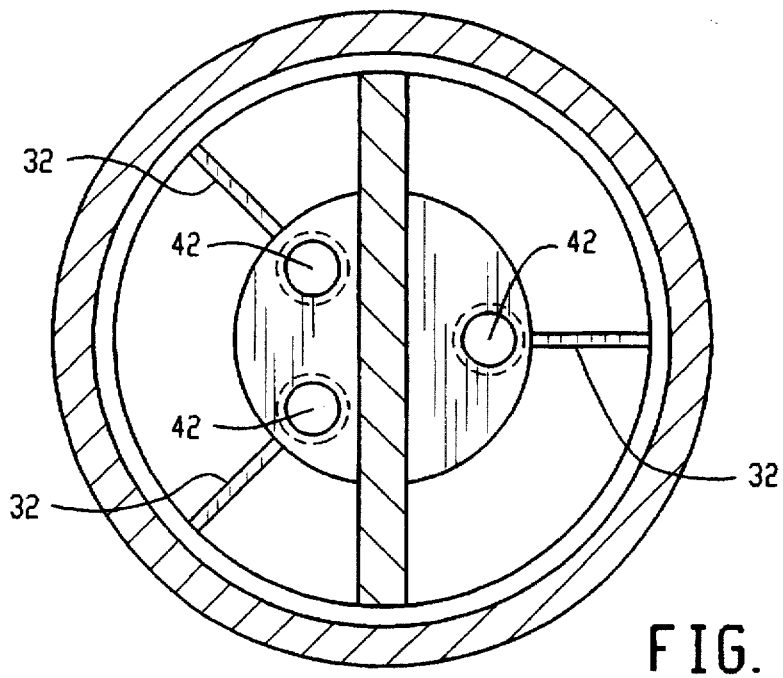
FIG. 2 is a plan view taken along the plane 2—2 in FIG. 1.

Turning now in more detail to the drawings and initially to FIGS. 1 and 2, a crystal assembly, indicated generally at 1, is contained or substantially contained within a probe tip housing 2 secured to the end of a tube 3. The crystal assembly 1, probe tip housing 2 and tube 3 cooperatively define a probe, indicated generally at 4. This probe may be used to analyze a sample by infrared energy absorption analysis.

The crystal assembly 1 includes a first crystal member 5 and a second crystal member 6. The first crystal member 5 includes a flat transmission surface 7 through which infrared energy enters and leaves the first crystal member 5. The first crystal member further includes a cylindrical portion which provides or defines a cylindrical surface 8 for mechanical positioning, alignment and sealing purposes. A cylindrical focusing surface 10 on the first crystal member extends from the cylindrical surface 8 to a flat optical interface surface 11. The transmission surface 7 and optical interface surface 11 of first crystal member 5 are parallel to one another and as flat as possible. The cylindrical surface 8 and circumferential focusing surface 10 are both surfaces of revolution formed about a common centerline 12.

The term circumferential focusing surface of a crystal member as used herein means at least one symmetrical surface of revolution about an optical axis or centerline 12 in which the radii thereof defining that surface of revolution vary in length along the optical axis as required to create a surface which is reflective, either as a result of the phenomenon of total internal reflection or as a result of overcoating the circumferential surface with a reflective material to be operative to redirect the infrared energy within the crystal material to and/or from a focal plane or ring. The circumferential focusing surface may be annular, two hemi-annular sections or two symmetrical and diametrically opposed partially annular sections. The circumferential focusing surface can be an inclined but flat surface, in elevation, such as formed by a frusto-conical section, or can be curved in elevation, such as formed from a portion of a paraboloid, ellipsoid, sphere, hyperboloid or other cylindrical surface of revolution defined by a higher order polynomial.

As shown in FIG. 1, the second crystal member 6 is a wafer thin disc having a flat optical interface surface 13 and a parallel flat sample contacting surface 14. The interface surface 13 on second crystal member 6 is in an optically transmissive relationship to the optical interface surface 11 on first crystal member 5. This optically transmissive interface between first crystal member 5 and second crystal member 6 may be accomplished in a number of different ways.

For example, first crystal member 5 and second crystal member 6 can be held together so that there is intimate contact between interface surfaces 11 and 13 to provide an optically transmissive interface therebetween. While flat surfaces are preferred for this optically transmissive interface, there may be some applications in which complementally curved interface surfaces are used to create the optically transmissive interface.

Alternatively, a thin layer or layers of a third crystal material, such as KeS-5 or silver chloride, can be interposed between first crystal member 5 and second crystal member 6. The third crystal member or material would abut and be in intimate surface contact with interface surfaces 11 and 13 to provide an optically transmissive interface therebetween.

The second crystal member 6 is preferably a diamond. The diamond material is chemically very resistant and is mechanically very strong. The index of refraction of the first crystal member 5 is matched as closely as possible to the diamond wafer forming the second crystal member 6. For this purpose, the first crystal member 5 could be formed from, Zinc selenide, zinc sulfide, KrS-5, sapphire, germanium, "AMTIR®" (which is a registered trademark for a chalcogenide glass material), silicon, silver bromide, silver chloride and cadmium telluride all of which have an index of refraction substantially the same as the index of refraction for diamonds. By using zinc selenide for the first crystal member and diamond for the second crystal member, benefits are obtained by having a less expensive and more easily formed member as the major focusing element and by having a more expensive and rugged member as the smaller sample contacting element.

While a diamond is the preferred material for second crystal member 6, it will be appreciated that the second crystal member could be formed from other materials, such as those listed above, as long as the indices of refraction for the first and second crystal members (and the third crystal member, if used) are substantially the same. The first and second crystal members could be the same material. By matching the indices of refraction in the infrared region of the electromagnetic spectrum as between the first and second crystal members and by providing an optically transmissive interface, the crystal assembly 1 allows optical energy to pass back and forth between the first and second crystal members where structurally permitted.

In this regard, the first crystal member can have a cavity 18 symmetrically formed therein about the optical center line 12. As shown, the cavity 18 extends inwardly into first crystal member 5 from interface surface 11. The cavity 18 in first crystal member 5 thus forms a void at the interface surface 13 of second crystal member 6 when the first and second crystal members are in assembled relationship. The diameter of the cavity 18 is smaller than the diameter of the first and second crystal members to define an annular ring radially outwardly of the void in which the two interface surfaces 11 and 13 are in intimate surface contact with one another to allow infrared energy to pass therebetween. The first and second crystal members are held in their assembled relationship within the probe tip housing 2 of probe 4.

The probe tip housing 2 has a generally cylindrical sidewall 20 and an end wall 21. The generally cylindrical sidewall 20 has an internally threaded section 22 adjacent its open end. The end wall 21 has an opening 23 to provide access to the second crystal member 6 and also has an internal flat 25 radially about the opening 23 to define a shoulder for receiving the outer peripheral portion of sample contacting surface 14 on second crystal member 6. The first and second crystal members 5 and 6 are tightly and reliably held in sealed relationship within the probe tip housing by an adjustment ring assembly indicated generally at 26.

The adjustment ring assembly 26 includes a first collar 27 having external threads 28. The external threads 28 on collar 27 mate with the internal threads on the internally threaded section 22 of the cylindrical sidewall 20 of the probe tip housing 3. This allows collar 27 to be threaded into the probe tip housing until it reaches the end of those internal threads. A spider mounting ring, indicated generally at 30, is positioned on the exposed end face of collar 27. This spider ring 30 includes an external circular ring 31 resting on the end face of collar 27, a plurality of thin spokes 32 connected to and extending radially inwardly from the circular ring and an adjustment ring body 33 secured to and supported by the radially extending spokes 32.

The spider mounting ring 30 may be clamped in position between the collar 27 and the end of tube 3. For this purpose, the end of tube 3 has a reduced diameter section 35 forming a radially outwardly extending shoulder 36. The outside diameter of the reduced portion 35 is threaded, as shown at 37. The threads 37 mate with the internal threads 22 on cylindrical sidewall 20 of probe tip housing 2. This threaded connection allows the tube 3 to be screwed into the probe tip housing until the leading end face on reduced diameter portion 35 engages or nearly engages the spider ring 30. During threaded advancement of the tube 3, the shoulder 36 engages a metal O-ring seal 39, which is tightly captured between the shoulder 36 and the top end surface 40 of probe tip housing 2. By threadedly coupling the tube 3 to probe tip housing 2, a fluid tight seal is formed by compressed O-ring seal 39, and the spider ring 30 is held in position properly to locate and hold the adjustment ring body 33.

The adjustment ring body 33 has three vertically extending and circumferentially spaced bores 42 which are internally threaded. The inner end of adjustment ring body 33 further includes a recess 43 at least partially receiving a pressure disc 44. The adjustment ring body 33 further has a slot 46 formed therein for intimately receiving the end of a partition 47. This slot 46 may include diametrically opposed side portions extending the full height of the adjustment ring body 33 and an interconnecting slot portion extending therebetween at the top of adjustment ring body. Such a generally U-shape slot configuration defined by the three slot portions receives and captures a similarly configured U-shape cutout on the end of partition 47. With such slot and groove interconnection, the leading or bottom end of partition 47 extends all the way into contact with the transmission surface 7 on first crystal member 5. This partition 47 bisects the inside of probe 4 to form an entry energy guide passage 48 and an exit energy guide passage 49 respectively leading to and from the crystal assembly 1, which is accurately positioned and sealed in the probe tip housing 2.

For this positioning and sealing, screws (not shown) are threadedly advanced in the circumferentially spaced bores 42 until the ends thereof simultaneously bear against the pressure disc 44. The adjustment screws are equally advanced to force the pressure disc 44 against the transmission surface 7 of first crystal member 5. This force is transmitted through first crystal member 5 to second crystal member 6. The advancement of pressure disc 44 thus results in the sampling surface 14 of second crystal member 6 being tightly pressed against flat 25 and also results in intimate contact between the first and second crystal members at the interface therebetween. In addition, the advancement of pressure disc 44 is operative to provide a fluid tight seal for and proper positioning and alignment of the crystal assembly 1.

In that regard, the probe tip housing 2 has two axially spaced annular grooves 51 and 52 respectively receiving resilient O-ring seals 53 and 54. These O-ring seals 53 and 54 bear against and are compressed by the cylindrical surface 8 on the cylindrical portion of first crystal member 5 to form a secondary or backup fluid tight seal between the first crystal member and the probe tip housing and to properly align or position the first crystal member within the probe tip housing. A further seal and alignment is provided adjacent the end of the probe tip housing by a third O-ring seal 56. This O-ring seal 53 is seated generally at the intersection between the generally cylindrical sidewall 20 and end wall 21 and bears against and is compressed by the circumferential reflecting surface 10 on first crystal member 5.

As is apparent from the above description, the adjustment ring assembly 26 and seals 53, 54 and 56 cooperate to properly position the crystal assembly 1 in sealed relationship within probe tip housing 2 in such a manner that intimate surface contact is achieved at the optically transmissive interface between first crystal member 5 and second crystal member 6 and between second crystal member 6 and the internal flat 25 on the probe tip housing 2. As thus assembled and sealed, the probe 4 with crystal assembly 1 can be used for optical analyzation of samples.

For this purpose, the sample contact surface 14 on second crystal member 6 is brought into contact with the sample to be analyzed. This sample can be a fluid, liquid, gel, paste, biological tissue, solid, etc. For sampling purposes, the probe, with its multiple fluid-tight seals, can be immersed in the sample material or can be manipulated so that the second crystal member comes into contact with the sample.

The optical analyzation system includes an energy source 58 which preferably provides a collimated beam 59 of infrared energy, preferably modulated, for FTIR sample analysis. As schematically shown in FIG. 1, the infrared beam 59 is reflected off inclined mirror 60 positioned at or near an image of the optical system's aperture stop to accept the source energy substantially in its entirety. The infrared energy reflected from mirror 60 is directed along inlet guide passage 48 in tube 3. The inlet guide passage 48 is filled with an energy transmissive medium, preferably dry air or purged gas, although a crystal material may also be used.

The transmissive medium in entry guide passage 48 has an index of refraction less than or equal to the indices of refraction for the first crystal member 5 and second crystal member 6. For example, the index of refraction for dry air is approximately 1, the index of refraction for zinc selenide is approximately 2.4 and the index of refraction for a diamond is approximately 2.4. By having the index of refraction in the transmissive media be less than the index of refraction in the first and second crystal members, any angle of divergence 61 in the rays of incoming infrared energy, which can approach up to an 8.5 degree angle of divergence, is reduced in its magnitude in first crystal member 5 in accordance with Snell's law. The index of refraction in the first and second crystal members is as high as possible in order to maximize this corrective effect in the crystal assembly. Preferably the collimated or nearly collimated energy beam or wavefront 59 is normal to transmissive surface 7 of first crystal 5 to optimize the energy throughput into the first crystal member 5 and to limit or eliminate any chromatic aberrations.

The infrared energy 59A within first crystal member is transmitted toward the focusing surface 10. The cylindrical surface 8 may be polished and can act as a mirrored wave guide to contain the energy within first crystal member 5. The infrared energy 59A reflects off the circumferential focusing surface 10 and is redirected at 59B to an annular focal ring or plane at or adjacent the optically transmissive interface between first crystal member 5 and second crystal member 6. This internal reflection off circumferential focusing surface 10 is accomplished by the phenomenon of total internal reflection when the angle of beam incidence to the surface is greater than the critical angle or by applying a reflective coating to the focusing surface. The circumferential focusing surface 10 may be potted in reflective material to obtain the internal reflection as well as mechanical alignment or positioning.

The focusing surface 10 is designed to maintain, to the extent possible, the imaging qualities of the source energy. In addition, the circumferential focusing surface can be used to control energy properties in the probe tip, such as angle, angular spread, shape and size, for the sample being analyzed. By focusing to the desired focal ring, the energy spread is minimized and the energy density and sensitivity are maximized.

Any stray energy from the focusing surface 10 that is not focused at this annular focal ring or plane may enter the cavity 18 and be absorbed therewithin. This cavity thus acts as a stray light or energy trap. The depth of the cavity 18 is selected to minimize stray infrared energy within first crystal member 5.

The focused infrared energy entering the second crystal member 6 internally reflects along the second crystal as indicated at 59C. In some applications, the infrared energy may reflect off the sample contacting surface only once before exiting the second crystal. In most applications however, the infrared energy will have multiple internal reflections or bounces along the second crystal member 6 before exiting.

Because of the angle of incidence and the void created by cavity 18, the infrared energy is totally internally reflected with minimal, if any, loss of energy at the interface surface 13 of second crystal 6. The interface surface 13 of second crystal member 6 can also be reflectively coated to optimize the energy internally reflected at that surface with or without the cavity.

At the sampling surface 14 of second crystal member 6, some infrared energy at certain bands will be absorbed into the sample on each reflection. The infrared energy absorbed is specific to the sample being analyzed, which results in the infrared energy reflected within the second crystal member being encoded with information characteristic of that sample. After traversing the cavity 18 with multiple internal reflections within the second crystal member 6, the encoded infrared energy exits the second crystal member 6 and reenters the first crystal member 5 at an annular focal ring or plane at or adjacent the interface between the first and second crystal members. The encoded infrared energy exits the second crystal member from a different portion of the interface surface 13 than where the infrared energy entered, with the entry and exit focal rings or planes being symmetrical about the optical centerline 12.

The encoded infrared energy 59D, which has reentered the first crystal body 5 reflects off of circumferential focusing surface 10 and is redirected as a collimated or nearly collimated beam 59E toward transmission surface 7 of first crystal member 5. This collimated beam 59E is normal or perpendicular to the transmissive surface 7 to optimize the energy passing from first crystal member 5 into output guide passage 49. The collimated and encoded beam of infrared energy 59F passes through the transmissive medium contained within output guide passage 49 and is reflected off of second mirror 62. Second mirror 62 is positioned at or near an image of the optical system's aperture stop so as to collect and reflect the encoded output energy substantially in its entirety. The reflected energy from second mirror 62 is directed to a detector 63. The detector processes the encoded infrared energy received and identifies the sample being analyzed by its infrared energy absorption characteristics.

As is apparent from the above description, the system is symmetrical about the partition 47. The input and output of infrared energy can be readily switched. In addition, the partition 47 can have both of its major surfaces mirrored to retain energy within the inlet and outlet guide passages. The mirrored divider retains separation between inlet and outlet energy and maximizes energy throughput in the optical system. This divider acts to minimize back reflected energy reaching the detector which could otherwise provide erroneous information about the sample.

The fluid tight probe 4 with the crystal assembly 1 has a small diameter and is improved for both sample analyzation and maintenance purposes. With respect to the fluid tight probe, the adjustment ring assembly 26 and axially spaced resilient and metal seals provide repeatable and accurate positioning of the probe tip components, fluid-tight probe integrity and chemical resistivity for the probe. With respect to the small diameter of the probe, in the preferred embodiment, the diameter of the probe tube is approximately $5/8$ in., the diameter of the first crystal member is approximately $1/2$ in., and the diameter of the second crystal member is approximately $1/4$ inch. The thickness of the second crystal is from $1/4$ to $1/2$ mm. With respect to operational advantages, the use of a diamond as the second crystal member allows the probe of this invention to be used with almost any sample no matter how corrosive. The diamond member 6 is also easily cleaned and maintained because it is resistant to scratching. With respect to further operational advantages, the probe utilizing the crystal assembly of the present invention enhances energy throughput and accuracy of sample analyzation for numerous reasons including selection of compatible crystal materials having matching indices of refraction greater than the index of refraction in the probe tube, utilization of at least one circumferential focusing surface, optimized energy transmission at the interface between the crystal members and optimized internal reflection within the second crystal member.

Figure 3:
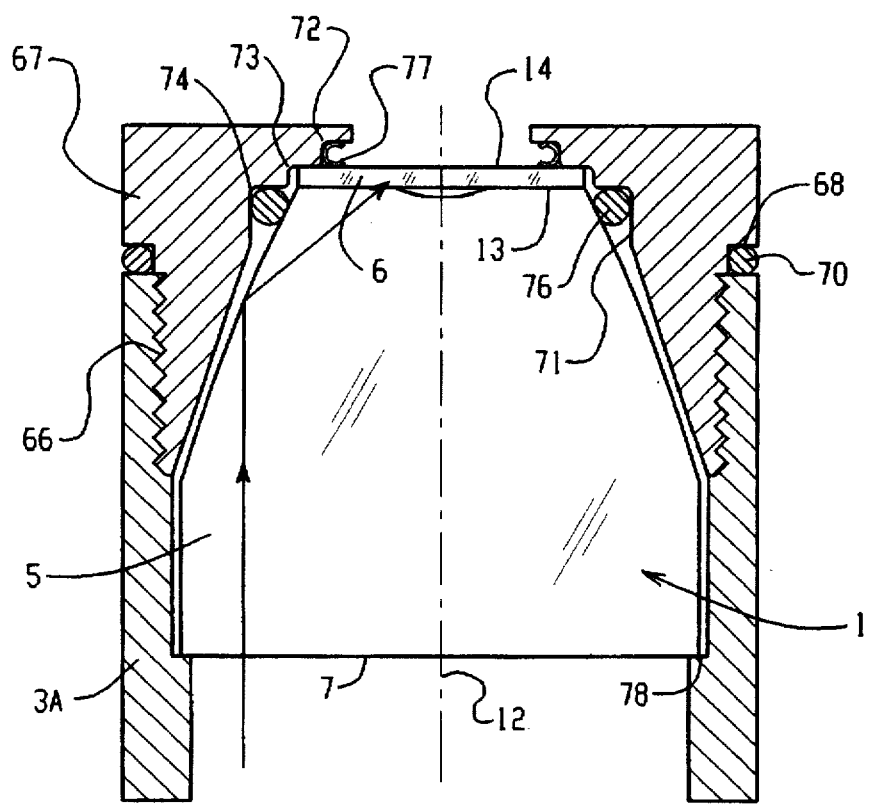
FIG. 3 is a partial cross-section of a crystal assembly resiliently mounted in another embodiment of a probe tip housing.

Turning now to FIG. 3, an embodiment for resiliently but tightly holding the crystal assembly in the probe tip is illustrated. The tube 3A has an internally threaded section 66 at its end. The threaded section 66 mates with external threads on an annular probe tip housing 67. The probe tip housing has a radially outwardly extending, annular shoulder 68 thereon. A metallic C-ring seal 70 is captured and compressed between the annular shoulder 68 and the end wall of tube 3A.

The probe tip body 67 includes a central, axially extending bore 71 that defines an opening providing access to the crystal assembly 1. The bore 71 includes a plurality of steps 72, 73 and 74 adjacent the probe tip. Step 73 receives the circumferential edge of second crystal member 6. Step 74 receives a resilient O-ring seal 76 which is compressed between the first crystal member 5 and the probe tip body to provide a fluid tight seal and proper crystal alignment. Step 72 receives a resilient metallic C-ring 77 which is captured between and compressed by step 72 and the sample contacting surface 14 of second crystal 6. A TELFON® or spring seal could be used instead of the metallic C-ring 77. "TEFLON®" is a registered trademark for a waxy, opaque material, polytetrafluoroethylene (PTFE), used as a coating to prevent sticking. By using a diamond wafer 6 as the second crystal member 6, a metallic seal can be employed, which may be desirable for certain corrosive or high temperature or pressure applications, without worrying about damaging or scratching the sample contacting surface.

The resilient C-ring 77 urges second crystal member 6 into intimate surface engagement with first crystal member 5, which is axially restrained or backed up by a stop shoulder 78. The C-ring 77 thus continuously maintains the first and second crystal members in intimate surface contact with one another to provide an optically transmissive interface therebetween. The resilient C-ring 77 provides for some limited movement of or between the first and second crystal members, which might occur in certain high temperature or pressure applications, but maintains an optically transmissive interface between the first and second crystals at all times.

Figure 4:
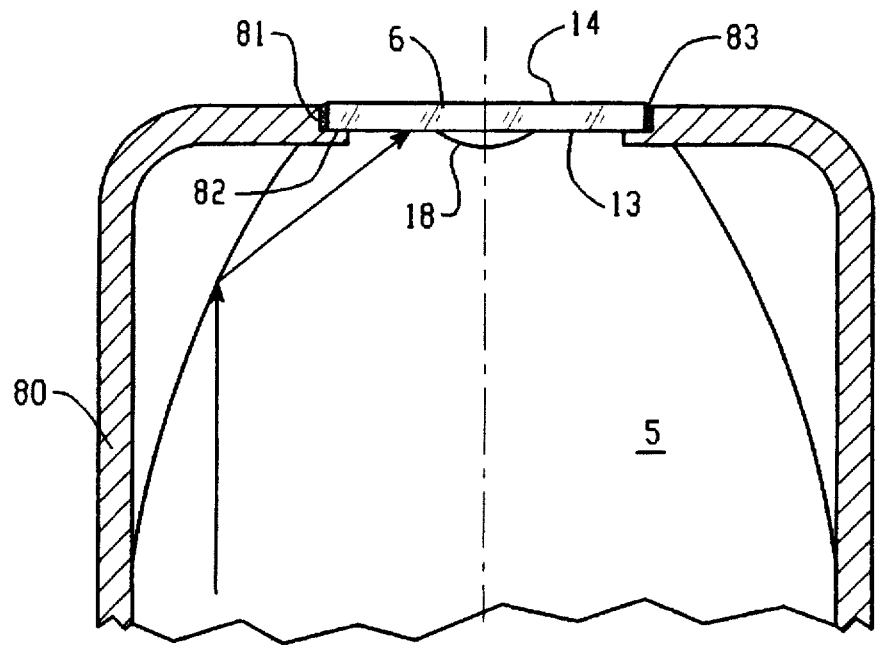
FIG. 4 is a partial cross section of another embodiment for mounting the crystal assembly, in which the sample contacting surface of the second crystal member is exposed at the end of the probe.

Turning now to FIG. 4, the crystal assembly 1 consisting of first crystal member 5 and second crystal member 6 is illustrated in a probe tip housing permitting the sample contacting surface 14 of the second crystal member 6 to be directly exposed to the sample. In this regard, and by way of comparison, the second crystal member 6 is recessed within the probe tip housing 80 in the embodiment of FIG. 1, but is situated to have at least the sample contacting surface 14 of second crystal member 5 positioned externally of the probe tip housing 80 in the embodiment of FIG. 4. For this purpose, the probe tip housing 80 includes a counter bore 81 at the end of the probe to define an externally facing shoulder 82. The second crystal member 6 has the outer circumferential portion of its interface surface 13 positioned on and resting against the externally facing shoulder 82. The second crystal member 6 is secured in that position by braising, molded plastic or epoxy 83 being received in the counterbore and positioned against and around the second crystal member 6. The first crystal member 5 may be held against the second crystal member 6 by the adjustment ring assembly 26 of FIGS. 1 and 2.

By mounting at least a portion of the second crystal member 6 externally of the probe tip, the sample contacting surface 14 thereof is exposed for immediate sample contact and for easy maintenance. This exposure of the sample contacting surface may insure better optical contact with some samples, such as biological tissue or other solids such as plastics. Other embodiments for having the sample contacting surface of the second crystal member exposed at the end of the probe are contemplated by the invention. For example, the probe tip housing could have an end opening larger than the second crystal received therewithin, with the crystal assembly being held in place by molded plastic or epoxy positioned between and secured to the crystal assembly and probe tip housing. Alternatively, the second crystal member can be curved to extend outwardly from the end of the probe or the second crystal member can be braised or welded to the probe tip housing or shrunk fit into the counterbore 81.

Figure 5:
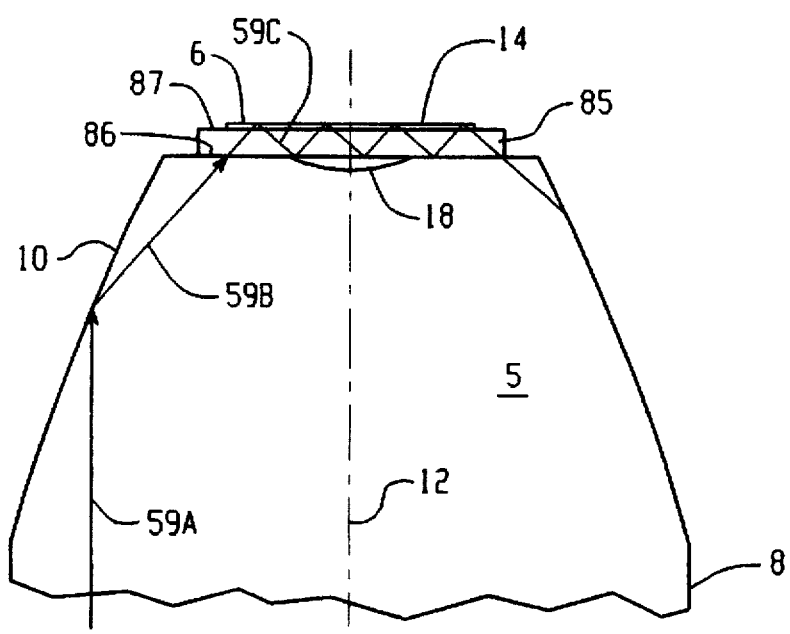
FIG. 5 is yet another embodiment of the crystal assembly according to the present invention employing three crystal members in the assembly, with the second and third crystal members being utilized for internal reflection to increase the path length of the infrared energy during sample contact.

In FIG. 5, the crystal assembly 1 includes a first crystal member 5, a second wafer thin crystal member 6, preferably a diamond disc, and a third crystal member 85 positioned therebetween. The crystal material for the third crystal member 85 is selected to have an index of refraction for infrared energy substantially matching the indices of refraction for first and second crystal members 5 and 6. As illustrated, the third crystal member 85 is a wafer disc which is thicker than the second crystal member 6. Third crystal member 85 has a first flat surface 86 in intimate surface contact with innerface surface 11 on first crystal member 5. The third crystal member 85 has a second flat surface 87 which is parallel to the first surface 86. Second flat surface 87 is in intimate contact with the interface surface 13 on second crystal member 6. The third crystal member 85 is held in intimate surface contact with first and second crystal members 5 and 6 by an adjustment ring assembly as described in the context of FIGS. 1 and 2 above, by a C-ring as described in the context of FIG. 3, by molded plastic, epoxy or braising as described in the context of FIG. 4 or by any other adjustable mechanism or housing structure operative to maintain intimate surface contact between the three crystal members to provide two optically transmissive interfaces therebetween.

In operation, transmitted infrared energy 59A within first crystal member 5 is redirected by cylindrical focusing surface 10 as shown at 59B toward an annular focal ring or plane at or adjacent the optically transmissive innerface between first crystal member 5 and third crystal member 85. The infrared energy then internally reflects within the third crystal member 85 and second crystal member 6 as shown at 59C. As illustrated, the infrared energy initially passes through the third crystal member 85 and second crystal member 6 to the sample contacting surface 14 where the non-absorbed or encoded infrared energy is reflected back through second crystal member 6 and third crystal member 85. The encoded infrared energy then reflects off of surface 86 adjacent cavity 18 and is thereafter successively internally reflected along the second and third crystal members. As illustrated, four bounces or reflections occur at the sample contacting surface, although one bounce or any number more than one bounce is contemplated by the invention depending upon the infrared energy wavelength being used and the sample being analyzed. After the last reflection off the sample contacting surface 14 when cavity 18 has been traversed, the encoded infrared energy passes back through the second crystal member 6, third crystal member 85 and then reenters the first crystal member 5 at a focal plane or ring to be redirected by cylindrical focusing surface 10 toward the detector.

By having the internal reflections occur within both the second and third crystal members for sample contacting purposes, the path length in the diamond is minimized but the overall path length is increased, so that it is possible to get encoded sample information in the full mid-infrared range of energy. In addition, the second crystal member 6 may be made of an even thinner diamond which reduces the cost of this probe. The three member crystal assembly may be used when the sample being analyzed falls in an infrared energy band or region requiring a longer path length than can be reflectively transmitted through the diamond wafer by itself.

Figure 6:
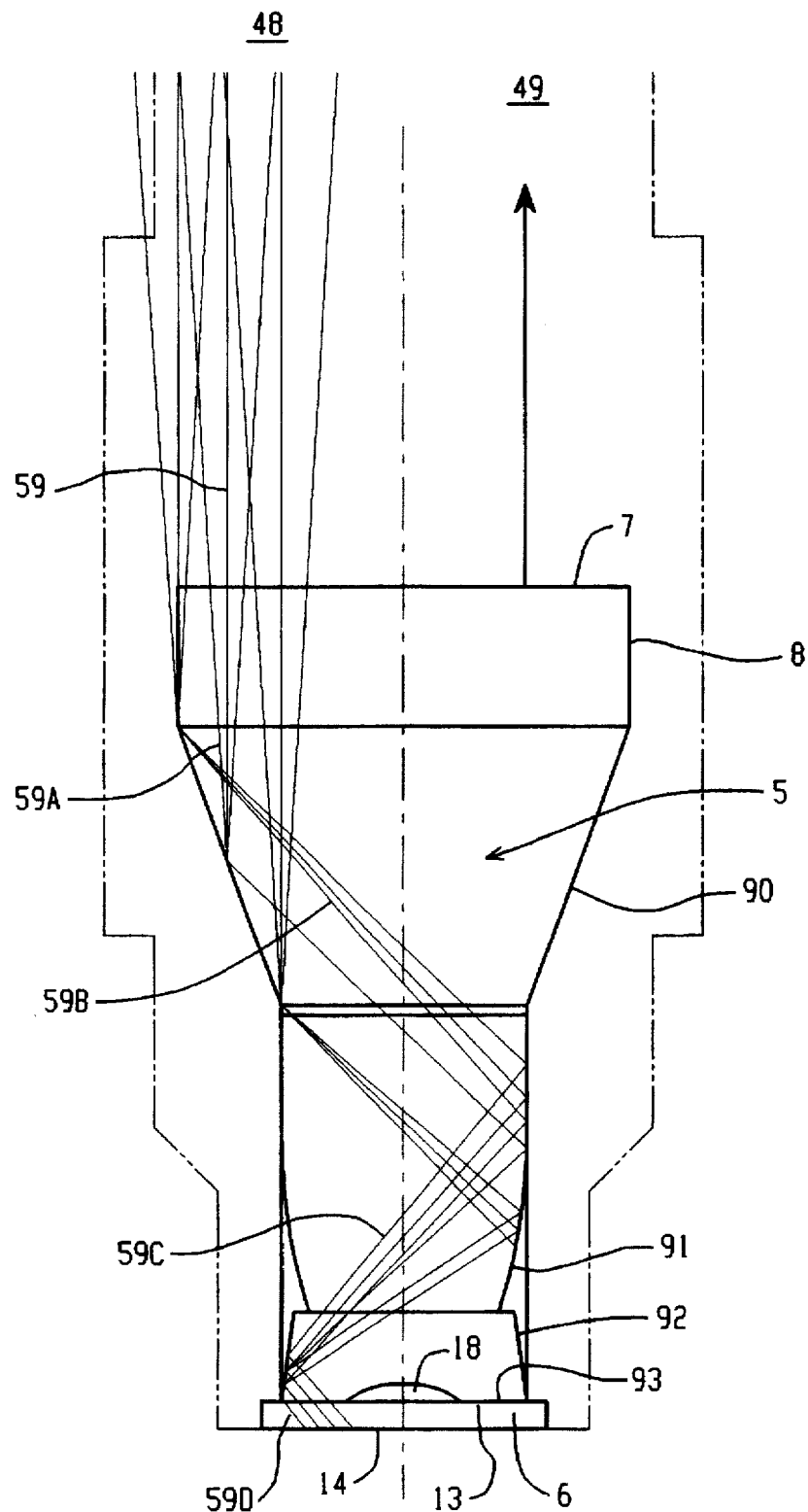
FIG. 6 is a cross section of still another embodiment of the crystal assembly according to the present invention in which the first crystal member has a plurality of circumferential focusing surfaces.

Turning now to FIG. 6, a crystal assembly having a first crystal member with multiple focusing surfaces is illustrated. The first crystal member 5 includes a flat transmission surface 7, a cylindrical sidewall surface 8 for guiding, sealing and alignment purposes, a first circumferential frusto-conical focusing surface 90, a second circumferential curved focusing surface 91, a third circumferential frusto-conical focusing surface 92 and interface surface 93. Transmission surface 7 and interface surface 93 are as flat as possible and parallel to one another. While all three circumferential reflective focusing surfaces 90, 91 and 92 are on an integrally formed first crystal member 5, it will be appreciated that multiple crystal members of the same crystal material cooperatively forming the same configuration could be used instead, as long as those multiple crystal members were held in intimate surface contact with one another to provide optically transmissive interfaces therebetween.

A second crystal member 6, preferably a thin diamond wafer, has its flat interface surface 13 held in intimate surface contact with interface surface 93 on first crystal member 5. A void or cavity 18 is provided at the end of the first crystal member 5 adjacent the optically transmissive interface between the first and second crystal members. The cavity diameter is less than the diameter of the flat innerface surface 93 to provide a radially outer annular ring for inputting and outputting infrared energy for sampling purposes.

In operation, the input infrared energy beam 59 is transmitted along inlet guide passage 48 and enters first crystal member 5 through flat transmission surface 7. The infrared energy 59A in first crystal member 5 is redirected by frusto-conical focusing surface 90 as shown at 59B toward the second curved reflective surface 91. While the frusto-conical focusing surface 90 does not focus the beam in all planes, it does focus the beam in a radial plane and provides a more dense beam concentration. The term "focusing surface" contemplates any surface that focuses the energy in at least one plane. The curved circumferential focusing surface 91 redirects the infrared energy as indicated at 59C toward a focal ring or plane at or adjacent the interface between the first and second crystal members. A third frusto-conical focusing surface 92 is interposed between the second curved focusing surface 91 and the optically transmissive interface to achieve the entry focal plane or ring at the desired geometric position. As is apparent from FIG. 6, the third frusto-conical focusing surface is reversed in its orientation from the first frusto conical focusing surface 90 to obtain the desired positioning of the focal ring or plane at the probe tip of a small diameter probe. All the focusing surfaces are surfaces of revolution about the centerline 12 and are thus positioned along the sidewall of the crystal member 5.

The infrared energy then internally reflects along the second crystal member 6 as indicated at 59D to obtain sample specific encoding. The infrared energy then exits at a focal ring or plane symmetrically opposed to the entry focal ring or plane. Such exiting infrared energy will sequentially be reflected off and be redirected by focusing surfaces 92, 91 and 90. The encoded infrared energy beam then leaves the first crystal member through flat transmissive surface 7 and is directed along outlet guide passage 49 ultimately to the detector 63. By utilizing three circumferential focusing surfaces 90–92, the length of the probe tip can be increased and/or the diameter of the probe can be decreased as may be required by certain sample applications.

Figure 7:
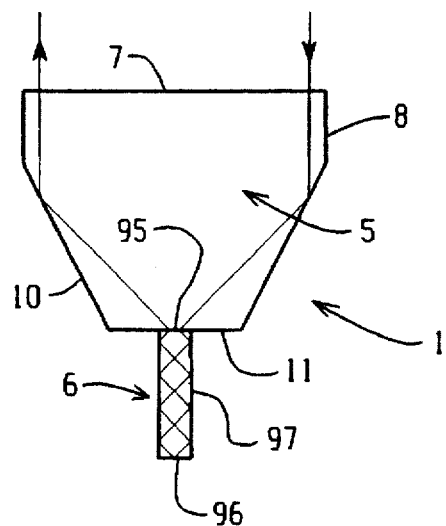
FIG. 7 is an additional configuration for the crystal assembly of the present invention adapted for a specific sampling environment.

Turning now to FIG. 7, an alternate crystal assembly 1 utilizing a differently shaped second crystal member is illustrated. The first crystal member 5 has a flat transmission surface 7, a cylindrical sidewall surface 8 for energy guiding, sealing and alignment purposes, a circumferential focusing surface 10 and a flat interface surface 11. The second crystal member, indicated generally at 6, is a diamond rod or fiber. The diamond rod has first end 95, second end 96 and a cylindrical sidewall 97 extending therebetween. The first end 95 of the diamond rod or fiber is held in intimate surface contact with interface surface 11 of first crystal member 5. The second end 96 and cylindrical sidewall 97 of the diamond rod or fiber are in contact with the sample during optical analyzation. The second end 96 of this rod or fiber is preferably curved to act as a reflective focusing surface for returning infrared energy along a separate path to increase energy throughput. As is apparent from the infrared energy path schematically illustrated, the cylindrical focusing surface 10 redirects the infrared energy to a focus at the second end 96 of the diamond rod or fiber. The infrared energy is internally reflected along the diamond rod or fiber until it reaches its focus at the second end 96. The infrared energy is reflected off end 96 and returns within diamond rod 6 along an exit path that is 180° from its path in entering the diamond rod 6. The infrared energy beam is encoded with sample specific information when it internally reflects off the interfaces between the cylindrical sidewall 97 or second diamond end 96 and the sample. The encoded infrared energy then returns or exits through first crystal member 5 along a path that is 180° from the infrared energy entry path.

Figure 8:
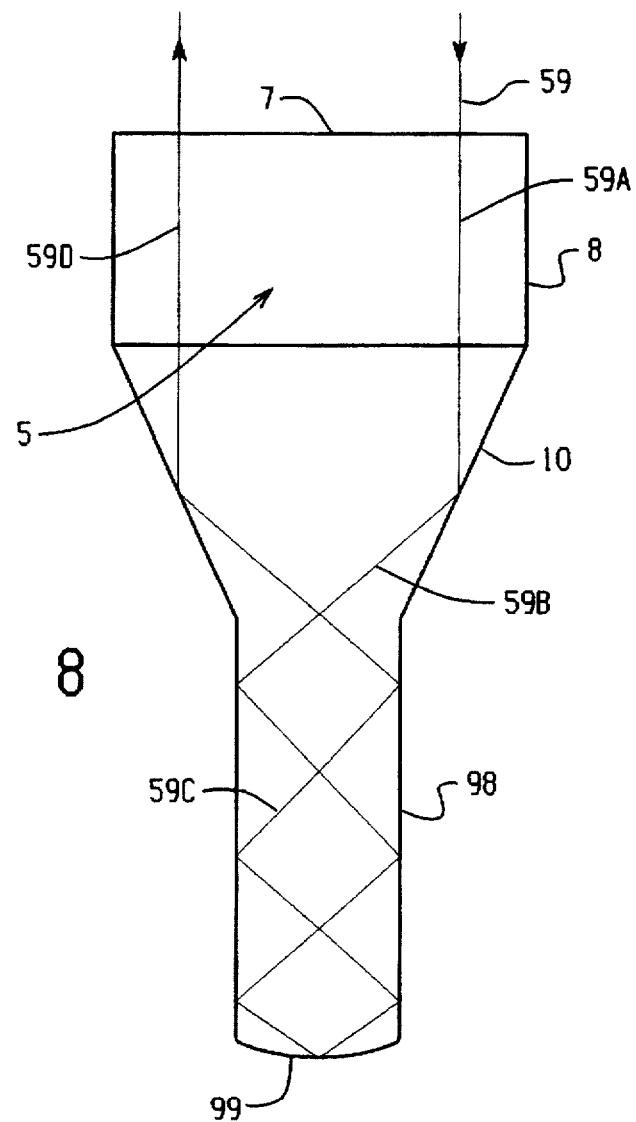
FIG. 8 is an elevation of a single crystal member having a first circumferential focusing surface and a second curved focusing surface adapted to contact the sample.

Turning now to FIG. 8, a single crystal member is illustrated which incorporates some of the features of the crystal assembly embodiment shown in FIG. 7. First crystal member 5 includes a transmission surface 7, a cylindrical surface 8, a circumferential focusing surface 10, a reduced diameter cylindrical extension having a cylindrical sidewall 98 and an end surface 99. The cylindrical extension 98 is integrally formed with the first crystal member 5, but is structurally similar to the diamond rod or fiber utilized as the second crystal member in FIG. 7. The end surface 99 is preferably curved as shown. The cylindrical extension 98 may be immersed or partially immersed in the sample.

The collimated or nearly collimated infrared energy 59 enters the first crystal member 5 through transmission surface 7. The infrared energy 59A within the first crystal member is reflected off circumferential focusing surface 10 and redirected toward a focus at or near the center of the end surface 99. Between the circumferential focusing surface 10 and surface 99, the infrared energy 59B is successively internally reflected along the cylindrical extension 98 which is in contact with the sample. This cylindrical extension provides extra length to the first crystal member 5 and also reduces the diameter of the sensing tip.

By being curved, the sample contacting surface 99 itself acts as a focusing surface to focus the circumferential focusing surface 10 back upon itself, but rotated 180°. As illustrated at 59C, the returning infrared energy internally reflects along the cylindrical extension 98, which is in contact with the sample, on a different path to the circumferential focusing surface 10. The infrared energy in the cylindrical extension is undergoing multiple bounces off the sidewall 98 and end wall 99, which are in contact with the sample. It will be appreciated that this crystal or the crystal assembly in FIG. 7 could also be used in applications in which only the end surfaces 99 and 96 are in contact with the sample.

The encoded returning infrared energy 59C is reflected off circumferential focusing surface 10 in a collimated or nearly collimated wavefront at a position substantially diametrically opposed to the entry energy. The infrared energy 59D reflected off of circumferential focusing surface 10 is directed back through the remaining parts of the system to the detector.

Figure 9A:
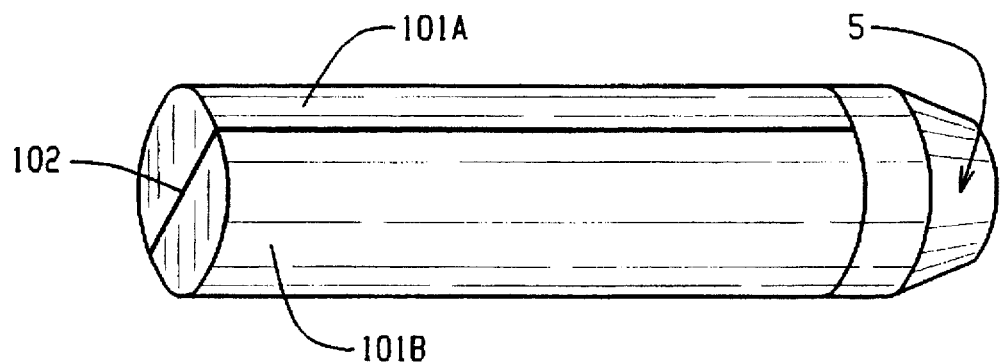
FIGS. 9A through 9C are perspectives showing different crystal assembly embodiments wherein the waveguides (or first crystal member) is constructed from component parts cooperatively coupled to create an effective partition between the entering and exiting infrared energy.
Figure 9B:
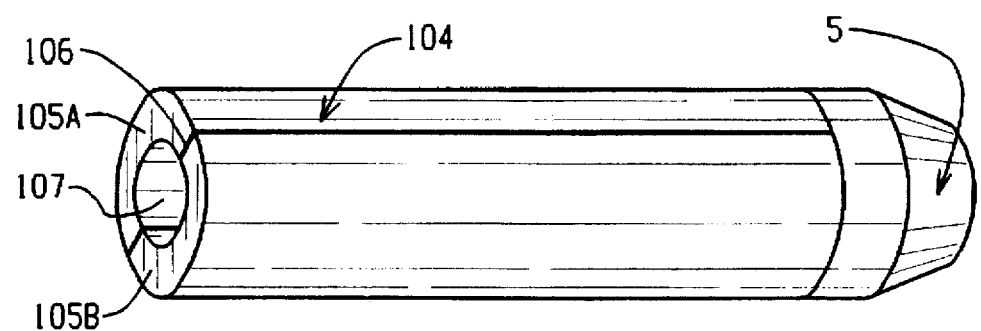
Figure 9C:
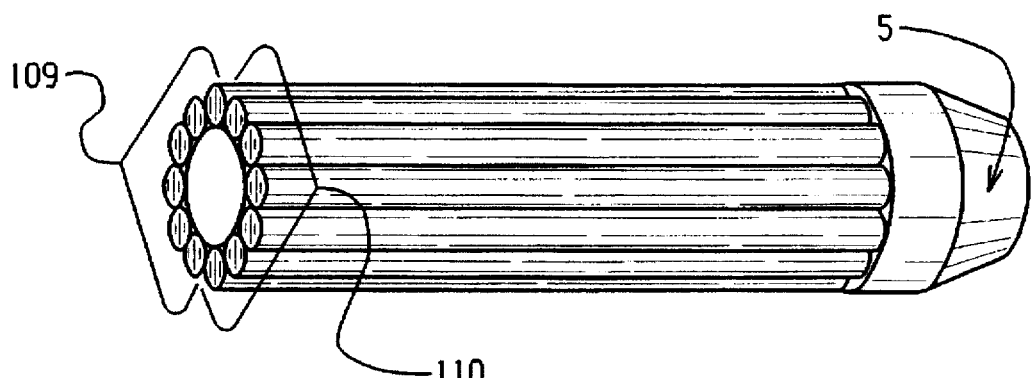

Turning now to FIGS. 9A through 9C, three embodiments are disclosed for providing an effective infrared energy partition in an elongated crystal assembly. With respect to FIG. 9A, the first crystal member 5 would be utilized with a second diamond disc at its right end (not shown). The tube 3 in this embodiment has been replaced by two identical crystal member sections 101A and 101B. Each such section is hemi-cylindrical in its configuration. The flat surfaces of the sections 101A and 101B are coated with a reflective material such as aluminum. The hemi-cylindrical sections 101A and 101B are then coupled together either mechanically or by epoxy, with their two flat and reflectively coated surfaces abutting one another as indicated at the interface 102. With the reflectively coated surfaces facing one another and the curved surfaces polished, the interface 102 becomes an energy partition and waveguide as between sections 101A and 101B.

Therefore, crystal member section 101A may act as an incoming or entry energy waveguide, and crystal member section 101B may act as an outgoing or exit energy waveguide. The interface 102 divides the two waveguides from one another and retains the energy in each of the respective waveguides. Because of the symmetry involved, either hemi-cylindrical section can act as an entry energy waveguide and either hemi-cylindrical section can act as an exit energy waveguide.

It will be appreciated that the two hemi-cylindrical sections 101A and 101B could each be formed adjacent one end to have at least one circumferential sidewall focusing surface thereon and a flat interface surface at that end. This would eliminate the need for a separate first crystal member as illustrated. A second diamond wafer would then be optically joined to these reflectively coated and coupled hemi-cylindrical sections to have a completed crystal assembly with a partition running all the way to the diamond interface. With this structure, the crystal assembly could be 3–5 inches long, or even longer, to provide a general purpose probe.

With respect to FIG. 9B, the crystal assembly may include two rolled silver chloride sheets, as indicated generally at 104. The first silver chloride sheet 105A is rolled into a hemi-cylindrical form, and the second silver chloride sheet 105B is also rolled into a substantially identical hemi-cylindrical shape. The rolled sheets 105A and 105B have their opposed end surfaces coated with reflective material. These reflectively coated surfaces are then brought into, or nearly into, abutment with one another as indicated by the interface 106. The rolled silver chloride sheet sections 105A and 105B act as energy guides to and from the first crystal member 5. The coated edges also act as a partition and energy guide. By using two hemi-cylindrically rolled sheets of silver chloride, the center of the abutting waveguides is filled with air, as indicated generally at 107.

Turning now to FIG. 9C, infrared energy can be brought to and collected from the first crystal member 5 by fiber optic bundles. A first bundle 109 formed in a hemi-cylinder array can be used as the infrared energy guide for delivery to the first crystal member 5 in optical contact therewith. A second hemi-cylindrically arranged bundle of fiber optics 110 can be used to collect encoded infrared energy from the first crystal member 5 in optical contact therewith for return to a detector.

It will be apparent from the foregoing that changes may be made in the details of construction and configuration without departing from the spirit of the invention as defined in the following claims.

We claim:

1. An optical analytical system having a source of infrared energy, an infrared detector system, and a crystal assembly comprising a first crystal member having at least one circumferential focusing surface, and a crystal disc,
    an optically transmitting interface between at least a portion of one surface of the first crystal member and at least a portion of an adjacent surface of the crystal disc,
    said crystal disc having a sample contacting surface which is opposite said optically transmitting interface,
    said source energy being redirected by a circumferential focusing surface, transmitted through said optical interface, and totally internally reflected in the second crystal at least once at the sample contacting surface, whereby said source energy obtains sample specific encoding; and
    said encoded source energy being transmitted from the crystal disc through the optically transmitting interface into said first crystal member and redirected by a circumferential focusing surface to the infrared detector system for sample analyzation.

2. The analytical system of claim 1 wherein the crystal disc is a diamond and the material of the first crystal member is selected to have an index of refraction for infrared energy substantially similar to the index of refraction for infrared energy of the diamond.

3. The analytical system of claim 1 wherein said source energy is totally internally reflected two or more times at the sample contacting surface.

4. The analytical system of claim 3 wherein the first crystal member has a cavity symmetrically formed therein adjacent the optically transmitting interface and sized to let infrared energy in and out of the crystal disc while permitting total internal reflection within the crystal disc between entry and exist.

5. The analytical system of claim 3 wherein at least a portion of the surface of said crystal disc adjacent to said optically transmitting interface is reflectively coated to optimize the energy reflected at that surface.

6. The analytical system of claim 1 wherein the optically transmitting interface comprises a third crystal member positioned between the first crystal member and crystal disc in intimate optically transmitting contact therewith.

7. The analytical system of claim 6 wherein the third crystal member is at least one thin layer deposited between the first crystal member and crystal disc.

8. The analytical system of claim 6 wherein the crystal disc is diamond, the first and third crystal members have an index of refraction substantially similar to the diamond and the third crystal member has one surface thereof adjacent the first crystal member at least partly reflectively coated to permit internal reflection of the infrared energy within the diamond and the third crystal member.

9. The analytical system of claim 1 wherein the first crystal member has a transmission surface through which infrared energy enters and leaves the first crystal member, and wherein said analytical system includes an energy waveguide containing a transmissive medium through which infrared energy passes before entering and after leaving the first crystal member, the first crystal member having a higher index of refraction than the transmissive medium to reduce infrared energy divergence angles in the first crystal member as compared to that present in the transmissive medium.

10. The analytical system of claim 9 wherein the transmission medium is divided by a partition extending at or near to the transmission surface of the first crystal member to define separate infrared energy entry and exit paths.

11. The analytical system of claim 10 wherein the crystal assembly is mounted on the end of a tube to form a sensing probe and the partition has mirrored surfaces on both sides and extends down the tube at or near its center.

12. The crystal assembly of claim 9 wherein the first crystal member includes a substantially cylindrical portion between the transmission surface and the circumferential focusing surface.

13. The analytical of claim 1 wherein two circumferential focusing surfaces are diametrically opposed to one another and have symmetrical arcuate surfaces in elevation.

14. The analytical system of claim 1 wherein the first crystal member has, in elevation, multiple circumferential focusing surfaces for sequentially redirecting infrared energy within the first crystal member.

15. The analytical system of claim 14 wherein the first crystal member has, in elevation, at least one curved circumferential focusing surface and at least one straight circumferential focusing surface for sequentially redirecting infrared energy within the first crystal member.

16. The analytical system of claim 1 wherein the first crystal member is formed by two symmetrical crystal hemi-cylindrical sections, which are coated with reflective material along their respective abutting and coupled surfaces cooperatively to form an infrared partition in the first crystal member.

17. The analytical system of claim 1 wherein said crystal assembly further comprises a first fiber optic bundle, in optical contact with said first crystal member, that acts as an energy waveguide to said first crystal member, and a second fiber optic member, in optical contact with said first crystal member, that collects encoded infrared energy from the first crystal member for return to a detector.

18. The analytical system of claim 17 wherein said first fiber optic bundle comprises a hemi-cylindrical array, and said second optic fiber bundle comprises a second hemi-cylindrical array.

19. The analytical system of claim 1 wherein the optically transmitting interface comprises two flat interface surfaces on the first crystal member and crystal disc in intimate optical contact with one another.

20. The analytical system of claim 19 wherein a tube is coupled to a probe tip body which houses the crystal assembly cooperatively to form a probe for the analytical system.

21. The analytical system of claim 20 wherein the diamond is positioned to at least partially extend beyond the probe tip body.

22. An optical analytical system having a source of infrared energy, an infrared detector system, and a crystal assembly comprising a first crystal member having at least one circumferential focusing surface, and a crystal disc, said crystal assembly further comprising a first rolled sheet of silver chloride that acts as an energy waveguide to said first crystal member and a second rolled sheet of silver chloride that acts as an energy waveguide from said first crystal member, an optically transmitting interface between at least a portion of one surface of the first crystal member and at least a portion of an adjacent surface of the crystal disc, said crystal disc having a sample contacting surface which is opposite said optically transmitting interface, said source energy being redirected by at least one of said circumferential focusing surfaces, transmitted through said optical interface, and totally internally reflected in the second crystal at least once at the sample contacting surface, whereby said source energy obtains sample specific encoding; and said encoded source energy being transmitted from the crystal disc through the optically transmitting interface into said first crystal member and redirected by at least one of said circumferential focusing surfaces to the infrared detector system for sample analyzation.

23. The analytical system of claim 22 wherein the opposed end surfaces of said first and second rolled sheets are coated with reflective material and brought into or nearly into abutment with one another.

24. Apparatus for optical analyzation of a sample with infrared energy, comprising a source of infrared energy, a detector and a crystal body having a circumferential focusing surface and one or more sample contacting surfaces wherein at least one of said sample contacting surfaces is curved to focus infrared energy focused by a first portion of the circumferential focusing surface back upon a second portion of said circumferential focusing surface so that infrared energy passing into and out of said crystal body is directed to and from diametrically opposed positions on said first and second portions of the circumferential focusing surface and the infrared energy is encoded with sample specific information at the sample contacting surface to permit analyzation of the sample at the detector.

25. The apparatus of claim 24 wherein said curved sample contacting surface comprises one end of a cylindrical extension from said crystal body.

26. The apparatus of claim 24, further comprising an energy waveguide associated with said crystal body and containing a transmissive medium through which infrared energy passes to and from said crystal body, the index of refraction of the crystal body being greater than the index of refraction for said transmissive medium.

27. The apparatus of claim 24 wherein said energy waveguide contains a transmissive medium through which infrared energy passes to and from said crystal body, the index of refraction of the crystal body being greater than the index of refraction for said transmissive medium.

28. A crystal assembly in an optical system to analyze a sample with infrared energy comprising:

a diamond disc having a sample contacting surface on one side of said disc and a first interface surface on another side of said disc opposite said sample contacting surface;

a first crystal member having a second interface surface positioned to form an .optically transmitting interface with said first interface surface on said disc;

said first crystal member having at least one circumferential focusing surface for redirecting infrared energy through said optically transmitting interface to permit the infrared energy to be internally reflected within said diamond disc to obtain sample specific encoding.

29. The crystal assembly of claim 28 wherein the material of the first crystal member is selected to have an index of refraction for infrared energy substantially similar to the index of refraction for infrared energy of the diamond disc.

30. The crystal assembly of claim 29 wherein the first crystal member has a transmission surface through which infrared energy enters and leaves the first crystal member, the infrared energy passing through a transmissive medium before entering and after leaving the crystal member, the crystal member having a higher index of refraction than the transmission medium to reduce infrared energy divergence angles in the first crystal member as compared to that present in the transmissive medium.

31. The crystal assembly of claim 28 wherein the optically transmitting interface comprises two substantially flat interface surfaces on said crystal member and diamond disc, in intimate optical contact with one another.

32. The crystal assembly of claim 28 wherein the optically transmitting interface comprises a third crystal member positioned between said first crystal member and diamond disc in intimate optically transmitting contact therewith.

33. The crystal assembly of claim 32 wherein the third crystal member is at least one layer deposited between the first crystal member and diamond disc.

34. The crystal assembly of claim 33 wherein the first and third crystal members have an index of fearaction substantially similar to the diamond disc and the third crystal member has one surface thereof adjacent the first crystal member at least partly reflectively coated to permit internal reflection of the infrared energy within the diamond disc and the third crystal member.

35. The crystal assembly of claim 28 wherein the first crystal member includes a substantially cylindrical portion between the transmission surface and the circumferential focusing surface.

36. The crystal assembly of claim 28 wherein a tube is coupled to a probe tip body which houses the crystal assembly cooperatively to form a probe for the optical system.

37. The crystal assembly of claim 36 wherein the diamond is positioned to at least partially extend beyond the probe tip body.

38. The crystal assembly of claim 28 wherein the first crystal member has a cavity symmetrically formed therein adjacent the optically transmitting interface and sized to let infrared energy in and out of the diamond disc member while permitting total internal reflection within the diamond disc between entry and exist.

39. The crystal assembly of claim 28 wherein the infrared energy passing within the diamond disc has a path length under going multiple internal reflections.

40. The crystal assembly of claim 28 wherein two circumferential focusing surfaces are diametrically opposed to one another and have symmetrical arcuate surface's in elevation.

41. The crystal assembly of claim 28 wherein the first crystal member has, in elevation, at least one curved circumferential focusing surface and at least one straight circumferential focusing surface for sequentially redirecting infrared energy within the first crystal member to the focal ring.

42. A crystal assembly for a radiant energy analytical system, comprising:

a first crystal member and a crystal disc, with an optically transmitting interface between said first crystal member and one face of said crystal disc, said crystal disc having a sample contacting surface on the opposite side of said disc from said interface; and said first crystal member having a circumferential focusing surface that redirects said radiant energy through said optically transmitting interface into said crystal disc so that said radiant energy is totally internally reflected within said crystal disc to obtain sample specific encoding.

43. The crystal assembly of claim 42 wherein said circumferential focusing surface comprises a portion of an outer surface of said first crystal member.

44. The crystal assembly of claim 43 wherein said circumferential focusing surface comprises frusto-conical section.

45. The crystal assembly of claim 43 wherein said circumferential focusing surface is curved in elevation.

46. The crystal assembly of claim 42 for an optical system to analyze a sample with infrared energy, wherein said crystal disc is a diamond and the material of said first crystal member is selected to an index of refraction for infrared energies substantially similar to the index of refraction for infrared energy of the diamond.

47. A crystal assembly in an optical system to analyze a sample with energy comprising:

a first crystal member having an optically transmitting interface a second crystal member;

said second crystal member having a sample contacting surface a side of said second crystal member opposite said interface;

the first crystal member having:
 a circumferential focusing surface for redirecting infarred energy through said optically transmitting interface; and
 a cavity adjacent the optically transmitting interface, said cavity being sized to permit said circumferential focusing surface to direct infrared energy through a first portion of said interface adjacent to said cavity so that said infrared energy is totally internally reflected within the second crystal member to obtain sample specific encoding and passes back through a second portion of the interface symmetrically opposed to said first portion of the interface.

48. The crystal assembly of claim 47 wherein said second crystal is a disc, said optically transmitting interface is on one side of said disc and the sample contacting surface is on the other side of said disc.

49. The crystal assembly of claim 48 wherein said optically transmitting interface comprises an annular ring around said cavity.

50. The crystal assembly of claim 49 wherein said cavity is symmetrically Formed about an optical center line of said first crystal member.

51. The crystal assembly of claim 47 wherein the second crystal member is a diamond and the material of the first crystal member is selected to have an index of refraction for infrared energy substantially similar to the index of refraction for infrared of the diamond.

52. A crystal for optical analyzation of a sample comprising at least one crystal body having a sample contacting surface and at least one circumferential curved focusing surface adapted to direct infrared energy to said sample contacting surface, said sample contacting surface being curved to redirect said infrared energy back upon a circumferential curved focusing surface so that infrared energy passing into and out of said crystal body is directed in substantially opposite directions to and from diametrically opposed positions on said circumferential curved focusing surface or surfaces.

53. An optical analytical system having a source of infrared energy, an infrared detector system, and an optical assembly comprising a first crystal member, one or more circumferential focusing surfaces, and a crystal disc, an optically transmitting interface between at least a portion of one surface of the first crystal member and at least a portion of an adjacent surface of the crystal disc, said crystal disc having a sample contacting surface which is opposite said optically transmitting interface, said source energy being redirected by one or more of said circumferential focusing surfaces, transmitted through said optical interface, and totally internally reflected in the second crystal at least once at the sample contacting surface, whereby said source energy obtains sample specific encoding; and said encoded source energy being transmitted from the crystal disc through the optically transmitting interface into said first crystal member and redirected by one or more of said circumferential focusing surfaces to the infrared detector system for sample analyzation.

54. The analytical system of claim 53 wherein two circumferential focusing surfaces are diametrically opposed to one another and have symmetrical arcuate surfaces in elevation.

55. The analytical system of claim 53 wherein the crystal disc is a diamond and the material of the first crystal member is selected to have an index of refraction for infrared energy substantially similar to the index of refraction for infrared energy of the diamond.

* * * * *

UNITED STATES PATENT AND TRADEMARK OFFICE
CERTIFICATE OF CORRECTION

PATENT NO. : 5,703,366

DATED : December 30, 1997

INVENTOR(S) : Donald W. Sting and Milan Milosevic

It is certified that error appears in the above-identified patent and that said Letters Patent is hereby corrected as shown below:

In column 3, line 21 and 22, "cylindrical focusing surface 10" should be -- circumferential focusing surface 10 --.

In column 3, line 65, "KeS-5" should be -- KRS-5 --.

In column 4, line 9, "from, Zinc" should be -- from zinc -- and "KrS-5" should be --KRS-5--.

In column 5, line 67, "53" should be -- 56 --.

In column 12, line 49, "a second diamond disc" should be -- a diamond disc --.

In claim 1, lines 56-57 of column 13, "optical interface" should be -- optically transmitting interface --.

In claim 1, lines 57-58 of column 13, "second crystal" should be -- crystal disc --.

In claim 7, line 22 of column 14, "thin" should be deleted.

In claim 12, line 50 of column 12, "crystal assembly" should be -- analytical system --.

In claim 13, line 54 of column 14, "analytical" should be -- analytical system --.

In claim 17, lines 8-9 of column 15, "second fiber optic member" should be -- second fiber optic bundle --.

In claim 21, lines 24-25 of column 15, "diamond" should be -- crystal disc --.

In claim 22, line 44 of column 15, "optical interface" should be -- optically transmitting interface --.

UNITED STATES PATENT AND TRADEMARK OFFICE
CERTIFICATE OF CORRECTION

PATENT NO. : 5,703,366

DATED : December 30, 1997

INVENTOR(S) : Donald W. Sting and Milan Milosevic

It is certified that error appears in the above-identified patent and that said Letters Patent is hereby corrected as shown below:

In claim 22, line 45 of column 15, "second crystal" should be -- crystal disc --.

Cancel claim 27, which is substantially duplicative of claim 26 and has no antecedent for "said energy waveguide".

In claim 34, line 54 of column 16, "fearaction" should be -- refraction --.

In claim 37, line 1 of column 17, "diamond" should be -- diamond disc --.

In claim 38, line 7 of column 17, "member" should be deleted.

In claim 41, lines 21-22 of column 17, "focal ring" should be -- optically transmitting interface --.

In claim 44, line 41 of column 17, "comprises frusto-conical" should be -- comprises a frusto-conical --.

In claim 46, line 47 of column 17, "selected to" should be -- selected to have --.

In claim 47, line 52 of column 17, "with energy" should be -- with infrared energy --.

In claim 47, line 54 of column 17, "interface" should be -- interface with --.

In claim 47, line 56 of column 17, "surface" should be -- surface on --.

In claim 47, line 60 of column 17, "infarred" should be -- infrared --.

In claim 48, line 8 of column 18, "crystal" should be -- crystal member --.

UNITED STATES PATENT AND TRADEMARK OFFICE
CERTIFICATE OF CORRECTION

PATENT NO. : 5,703,366

DATED : December 30, 1997

INVENTOR(S) : Donald W. Sting and Milan Milosevic

It is certified that error appears in the above-identified patent and that said Letters Patent is hereby corrected as shown below:

In claim 51, line 21 of column 18, "infrared" should be -- infrared energy --.

In claim 53, line 45 of column 18, "optical interface" should be -- optically transmitting interface --.

In claim 53, line 46 of column 18, "second crystal" should be -- crystal disc --.

Signed and Sealed this

Twenty-eighth Day of April, 1998

Attest:

BRUCE LEHMAN

Attesting Officer

Commissioner of Patents and Trademarks